(12) United States Patent
Millet et al.

(10) Patent No.: US 7,259,571 B2
(45) Date of Patent: Aug. 21, 2007

(54) DETECTOR OF OBJECTS BY MICROWAVE FREQUENCY ECHO ANALYSIS

(75) Inventors: Nicolas Millet, Villebon sur Yvette (FR); Jean-Claude Lehureau, Sainte Genevieve des Bois (FR)

(73) Assignee: Thales, Neuilly sur Seine ( * ) Notice: Subject to any disclaimer, the term of this patent is extended or adjusted under 35 U.S.C. 154(b) by 0 days.

(21) Appl. No.: 11/435,281

(22) Filed: May 17, 2006

(65) Prior Publication Data

US 2007/0001689 A1    Jan. 4, 2007

(30) Foreign Application Priority Data

May 24, 2005    (FR)    ................................... 05 05208

(51) Int. Cl.
*G01R 27/32*    (2006.01)
(52) U.S. Cl. ...................................... 324/639; 324/637
(58) Field of Classification Search ................ 324/639, 324/637
See application file for complete search history.

(56) References Cited

U.S. PATENT DOCUMENTS

| | | | |
|---|---|---|---|
| 6,353,224 B1 | 3/2002 | Sinclair et al. | |
| 6,359,582 B1 * | 3/2002 | MacAleese et al. | .......... 342/22 |
| 6,777,684 B1 | 8/2004 | Volkov et al. | |
| 6,856,271 B1 * | 2/2005 | Hausner | ....................... 342/22 |
| 6,937,182 B2 * | 8/2005 | Lovberg et al. | ............... 342/22 |
| 6,950,054 B1 * | 9/2005 | Steinway et al. | ............. 342/22 |
| 7,119,731 B2 * | 10/2006 | Fleisher | ....................... 342/22 |

* cited by examiner

*Primary Examiner*—Walter Benson
(74) *Attorney, Agent, or Firm*—Lowe Hauptman & Berner, LLP

(57) ABSTRACT

The field of the invention is that of devices for detecting non-metallic objects concealed on human subjects. These devices are more particularly dedicated to the surveillance and protection of reserved access areas, such as airport areas. The device according to the invention comprises a portable detector comprising a transmitter and a receiver of microwave frequency signals disposed in an enclosure of chaotic geometry including a plurality of measurement holes. The microwave frequency signal measured by this detector depends on the nature of the objects disposed under the holes. A processing device linked to this detector is used to correlate the measured signals with prerecorded signals. When the correlation exceeds a certain threshold corresponding to the presence of suspect objects, an alarm is generated.

14 Claims, 10 Drawing Sheets

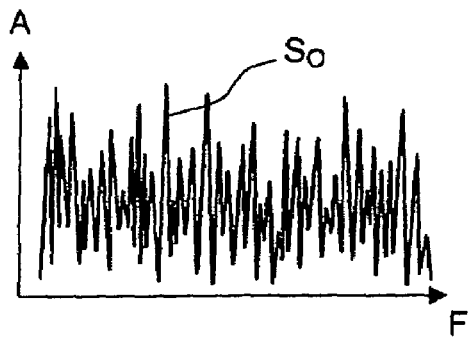
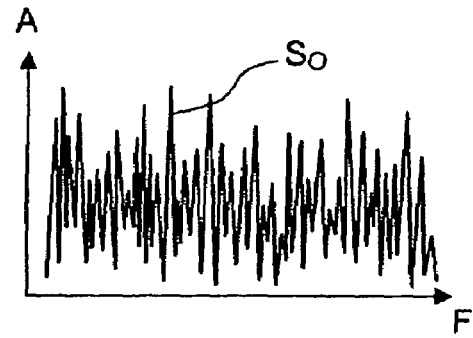
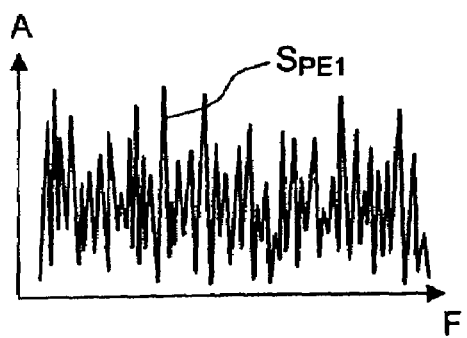
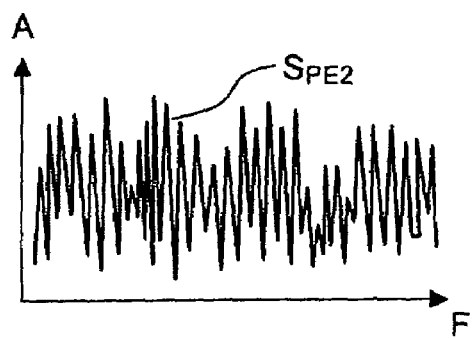
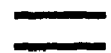
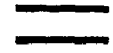
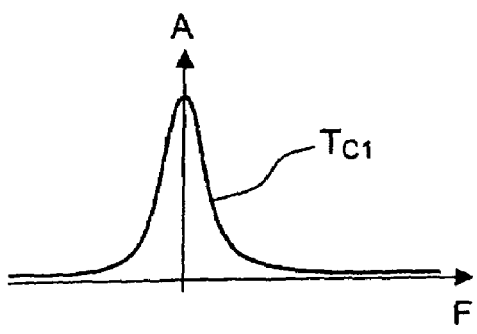
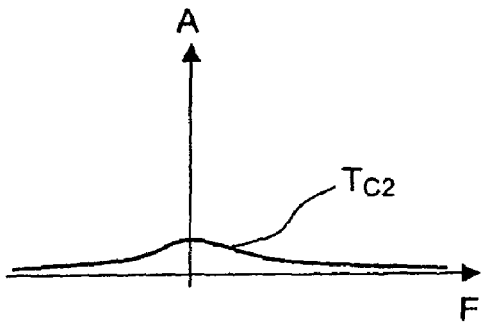
FIG.10                                   FIG.11

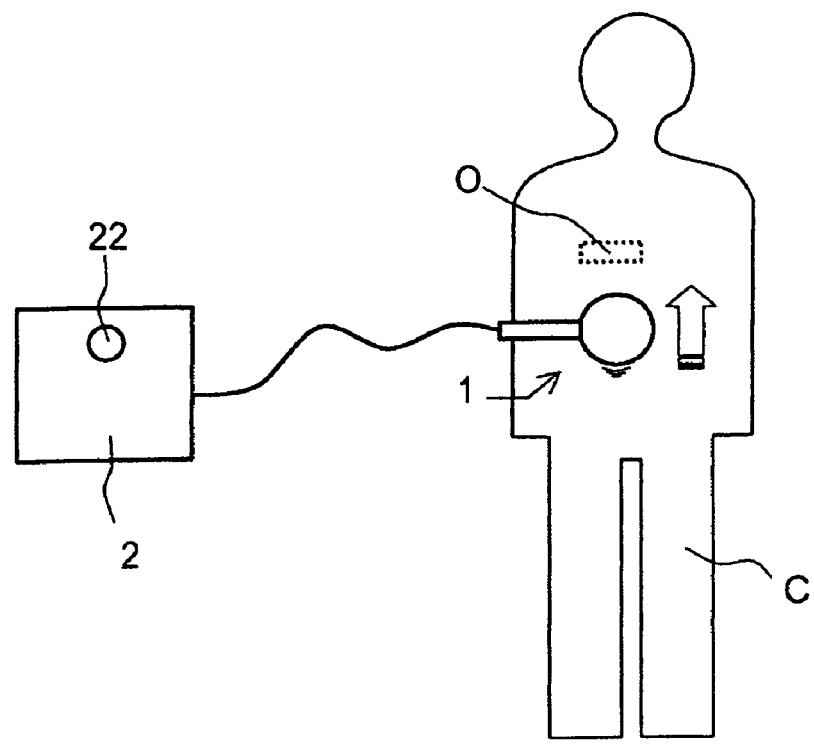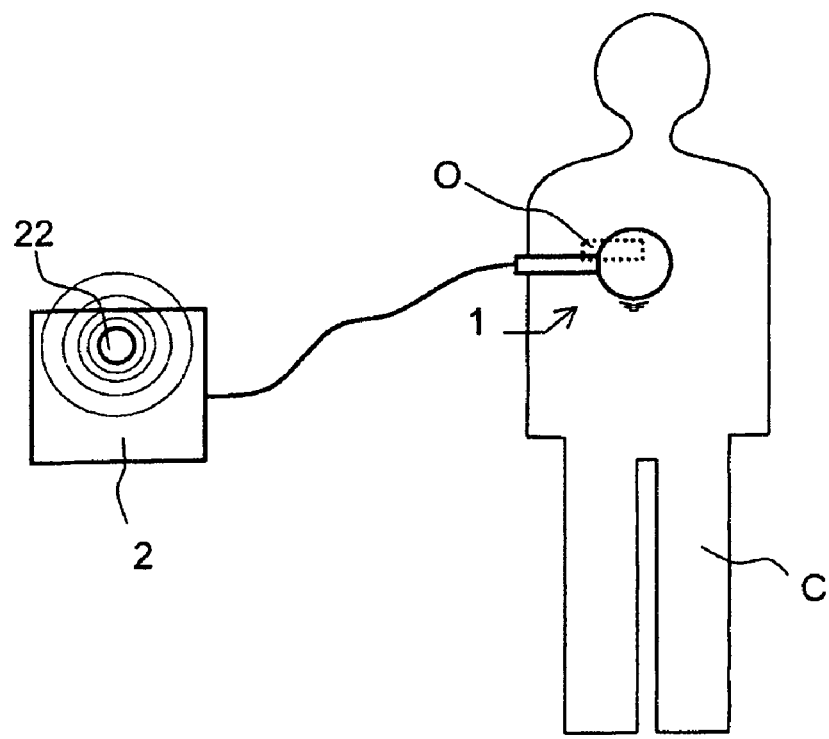
FIG.16

DETECTOR OF OBJECTS BY MICROWAVE FREQUENCY ECHO ANALYSIS

BACKGROUND OF THE INVENTION

1. Field of the Invention

The field of the invention is that of devices for detecting objects concealed on human subjects. These devices are more particularly dedicated to the surveillance and protection of airport areas and transport airplanes, but can also be positioned at the entrance of protected buildings or controlled access areas such as boat or train embarkation platforms.

2. Description of the Prior Art

To ensure the safety of the passengers in aircraft, cargo hold luggage and hand baggage is checked by X-ray imaging systems. The passengers themselves pass only through a metal-detector gate. Now, it is essential to detect on a passenger non-metallic objects that present a real danger such as explosives or ceramic weapons.

To overcome this security omission, some airports have put in place, experimentally, X-ray scanners for the passengers themselves. However, the use of X-rays for a non-medical purpose is prohibited in a large number of countries and in particular in most European states. In practice, this technique includes a real danger for the human being when exposed to regular use.

To overcome the drawbacks of using X-rays, it is possible to take an image of the human body in the field of millimetric electromagnetic waves. In practice, the objects or dangerous materials that we are trying to detect reflect the waves in a manner that is very different from that of the human body. This means they can easily be detected. This imaging can be done either passively, or actively. The passive technique consists in taking an image directly of the body without illuminating it with a particular millimetric source. In contrast to this, the active technique can be used to take an image by illuminating the body, for example, with a known millimetric beam with a precise wavelength.

These techniques have a number of drawbacks. They are complex to implement. Some use costly mirror-deflection systems. Systematically installing them in an airport therefore involves considerable investments. Also, the techniques consisting in taking the image of the human body come up against an ethical problem. In practice, since clothes are not very dense and are unconstructed, they are transparent to the millimetric radiation and, consequently, the subject appears nude on the millimetric image. Now, the passenger will not accept being analyzed nude by an operator.

To overcome these drawbacks, it is possible to simplify the systems by using small portable devices which make it possible to scan the observed body without taking images. Normally, these devices take a measurement of the power reflected by the human body as a function of the frequency of the transmitted wave. This is used to determine the significant electromagnetic resonances that reveal the presence of dielectric objects. It is also possible to have the detection based on measurements of polarization or ellipsometry of the waves reflected by the human body, the polarization characteristics depending on the nature of the illuminated body. One of the main drawbacks of these single-detector systems is that the measurement is a spot or almost spot measurement. Consequently, checking a subject can take some time. These devices are ill-suited to quickly checking a large number of passengers. It can also be difficult to determine very accurately the position or the size of a suspect object.

SUMMARY OF THE INVENTION

The proposed device largely resolves these drawbacks. In practice, it can be used to perform a simultaneous measurement at several points from a single transmitter and detector pairing. Thus, a large check area can be covered without taking an image while fairly accurately locating a suspect object, so facilitating the intervention of a security agent for a more thorough investigation. Furthermore, the millimetric waves used by this device do not present any hazards to human health and therefore can be used widely. Analyzing signals does not require significant computation power and conventional computer resources are sufficient for this purpose. In the end, this device offers great simplicity and can be produced inexpensively.

The physical principle implemented is based on the variations of a microwave frequency signal transmitted inside an enclosure including a certain number of holes designed to allow the electromagnetic waves to leak. When one of these holes is in the vicinity of or in contact with a body, the leaks generated by this hole vary according to the reflection properties of this body. Consequently, the geometry of the enclosure is disturbed and, of course, the microwave frequency signal is modified. By analyzing this signal, the location of the disturbance can thus be found. Naturally, for the device to operate correctly, it is essential for the disturbance of each hole to be significant and decorrelated from those of the other holes. For this, it is necessary for the geometry of the enclosure to be chaotic as will be seen in the rest of the description.

More specifically, the subject of the invention is a device for detecting dielectric objects on a human body comprising at least one detector with an enclosure in which are disposed a wave transmitter transmitting a microwave frequency signal and a microwave frequency receiver, said enclosure including a measurement surface intended to be positioned in the vicinity of said human body, wherein said enclosure is highly reflective to the waves transmitted by the transmitter, has a chaotic type geometry for said waves and wherein the measurement surface includes at least two holes.

Advantageously, the detector includes a single transmitter also serving as the receiver, the enclosure has essentially flat walls, flat reflectors are disposed inside the enclosure, a dielectric guide links the transmitter and the receiver so as to provide a reference signal to the receiver and waveguides are disposed in line with the holes to facilitate the leakage of the waves transmitted by the transmitter towards the outside of the enclosure.

Advantageously, the detector is portable and its structure includes, to this end, a handle. Also, the spectrum of the transmitted signal has a width of a few gigahertz in the 18 to 40 gigahertz frequency range.

Advantageously, the device includes an electronic data processing system including means:

Of memorizing prerecorded signals corresponding to the various open or closed states of the holes;

Of acquiring the signals received by the detector;

Of processing said received signals;

Of correlating said processed signals with the various prerecorded signals;

Of warning when the correlation ratio between a processed signal and at least one of the prerecorded signals exceeds a critical threshold, said warning means being audible or visual.

The invention also relates to a method of detecting dielectric objects on a human body from a detection device including the above characteristics, which includes, at least, the following successive steps:

Step 1: Production of prerecorded received signals corresponding to the various open or closed states of the holes;
Step 2: Positioning of the detector in the vicinity of a human body;
Step 3: Acquisition of the received signal corresponding to this location of the detector and processing of said received signal;
Step 4: Correlation of said processed signal with the various prerecorded signals;
Step 5: Transmission of a warning signal when the correlation ration between the processed signal and at least one of the prerecorded signals exceeds a critical threshold.

Advantageously, the first step of the method includes the following substeps:

Substep 1: With the holes of the enclosure all open, transmission of a frequency ramp by the transmitter;
Substep 2: Recording of the received frequency signal, said signal being denoted enclosure frequency-signal;
Substep 3: With at least one of the holes closed, transmission of a frequency ramp by the transmitter;
Substep 4: Recording of the received frequency signal, said signal being denoted hole-frequency-signal;
Substep 5: Calculation of a prerecorded signal obtained by subtraction of the enclosure-frequency-signal from the hole-frequency-signal;
Substep 6: Execution of substeps 3 to 5 for the various open or closed states of the holes so as to obtain the various prerecorded signals.

Advantageously, the third step includes the following substeps:

Substep 1: Transmission of an electromagnetic frequency ramp by the transmitter;
Substep 2: Recording of the received frequency signal called measurement-frequency-signal corresponding to said transmission signal;
Substep 3: Calculation of the processed signal obtained by subtraction of the enclosure-frequency-signal from the measurement-frequency-signal.

BRIEF DESCRIPTION OF THE DRAWINGS

The invention will be better understood and other advantages will become apparent from reading the description that follows, given by way of nonlimiting example and with reference to the appended figures in which:

FIGS. 10 and 11 represent the detection principle based on the correlation of a measured signal with the prerecorded signals;

FIG. 16 represents the implementation of a detection system according to the invention.

MORE DETAILED DESCRIPTION

Figure 1:
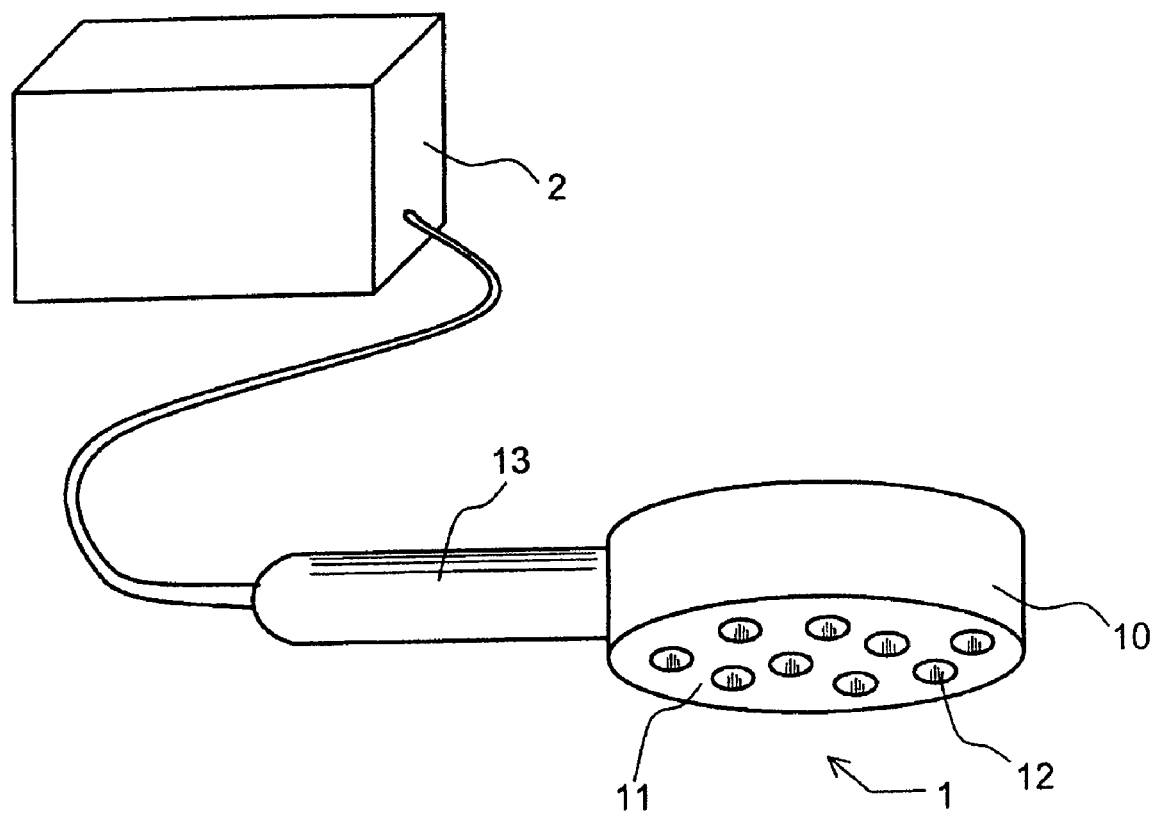
FIG. 1 represents a view of a device according to the invention including the detection means proper.

FIG. 1 represents a view of the detection system according to the invention. It essentially comprises two main elements:

a detector 1 comprising a system for transmitting and receiving microwave frequency signals;
an electronic data processing system 2 linked to said structure.

Externally, the structure of the detector 1 essentially comprises:

an enclosure 10 with a measurement surface 11 designed to be positioned in the vicinity of the human body, said surface 11 having a certain number of holes 12;
a handle 13 or any other handling means for manipulating the structure.

Figure 2:
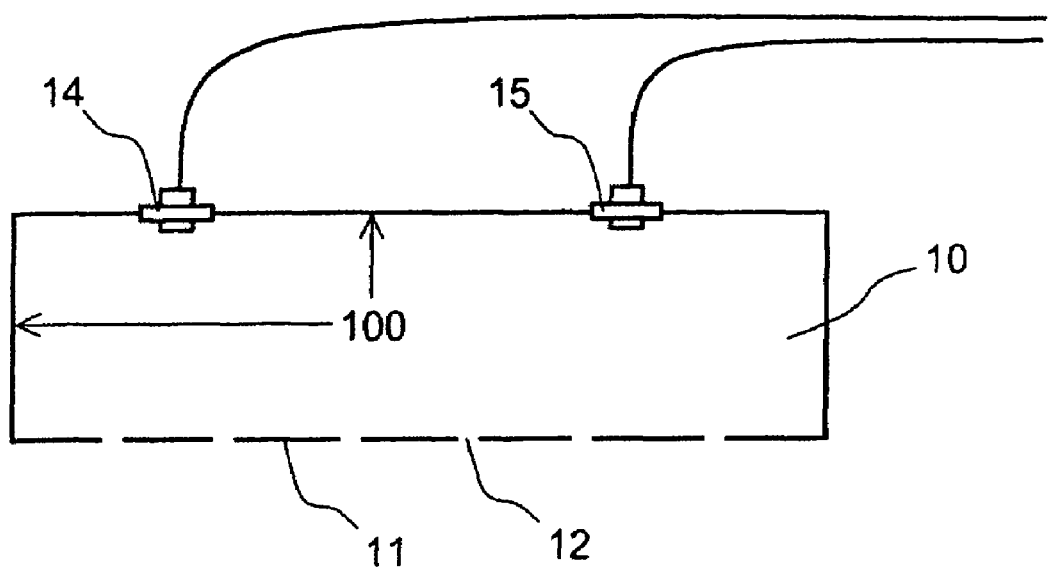
FIG. 2 represents a cross-section view of the enclosure of the detection structure.
Figure 3:
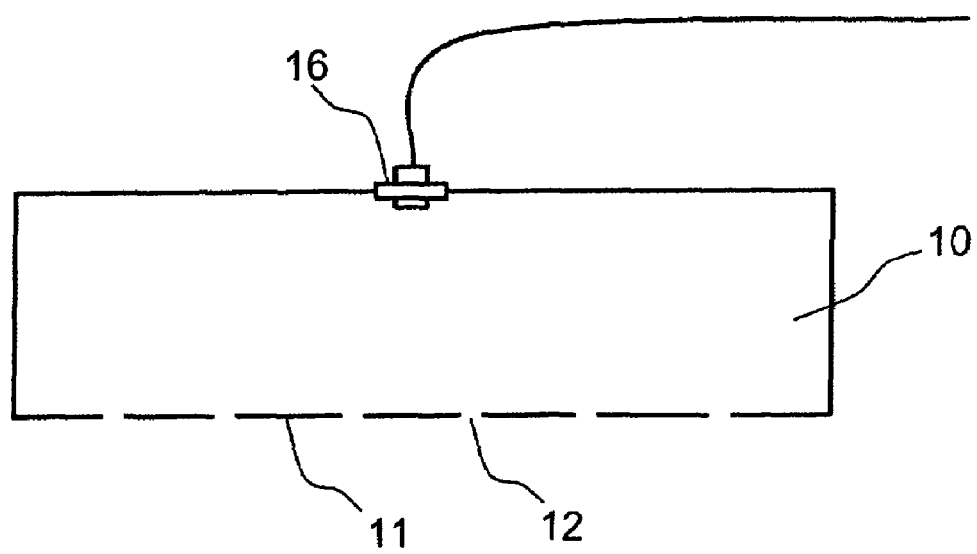
FIG. 3 represents a first variant of an embodiment of said enclosure.

FIG. 2 represents a first cross-section view of the enclosure 10. This enclosure mainly comprises walls 100 reflecting the millimetric waves, a measurement surface 11 with holes 12. A microwave frequency transmitter 14 and a receiver 15 are disposed inside the enclosure. As indicated in FIG. 3, the transmitter and the receiver can be combined in a single transceiver device 16.

Figure 4:
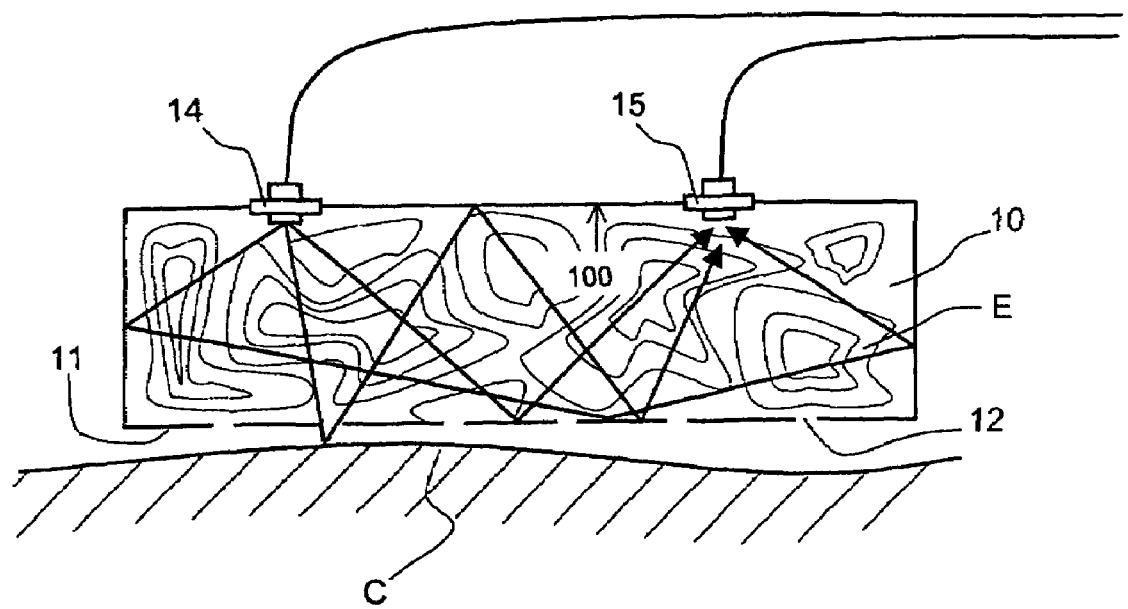
FIG. 4 represents the electromagnetic energy distribution inside said enclosure.

The operating principle is as follows. The detector is disposed in front of an object C as indicated in FIG. 4. The transmitter 14 transmits an electromagnetic pulse in the microwave frequency range inside the enclosure 10. More specifically, the spectrum of the transmitted signal has a width of a few gigahertz in the 18 to 40 gigahertz frequency range. As indicated in FIG. 4, since the walls 100 of the enclosure are highly reflective, the signal is subject to numerous reflections before arriving at the detector. These reflections are symbolized by the three arrow lines in FIG. 4. The enclosure is filled with energy as indicated by the fine-lined curves in FIG. 4 which correspond to the equal energy curves. A portion of the signal is also received via the holes 12. Depending on the nature of the object C placed in front of these holes 12, this portion will be lost or reflected inside the enclosure. In practice, the human body is highly reflective in the frequency domain used. Mainly consisting of water with a complex index of approximately 6+3i, the reflection coefficient of the human body is approximately 70%. Conversely, the dielectric bodies have lower reflection coefficients. In the rest of the text, the hole is said to be open if the energy is mostly lost and closed if the energy is mostly reflected inside the enclosure.

Consequently, the signal arriving at the receiver depends both on the geometry of the enclosure and on the nature of the body placed in front of the holes. For the signal to be usable, it is essential for two conditions to be satisfied:

the variation of the signal due to change of state of a hole must be significant;
the signal variations due to two different holes must be substantially different so as to easily differentiate the holes.

To combine these two conditions, the cavity must be of chaotic type so as to render it highly sensitive to weak disturbances and in particular to the changes of state of the holes. In these conditions, the percussive response of the cavity is therefore extremely disordered. A large quantity of pulses arrive at the transmitter at more or less long intervals after a more or less complex path inside the enclosure 10.

Figure 5:
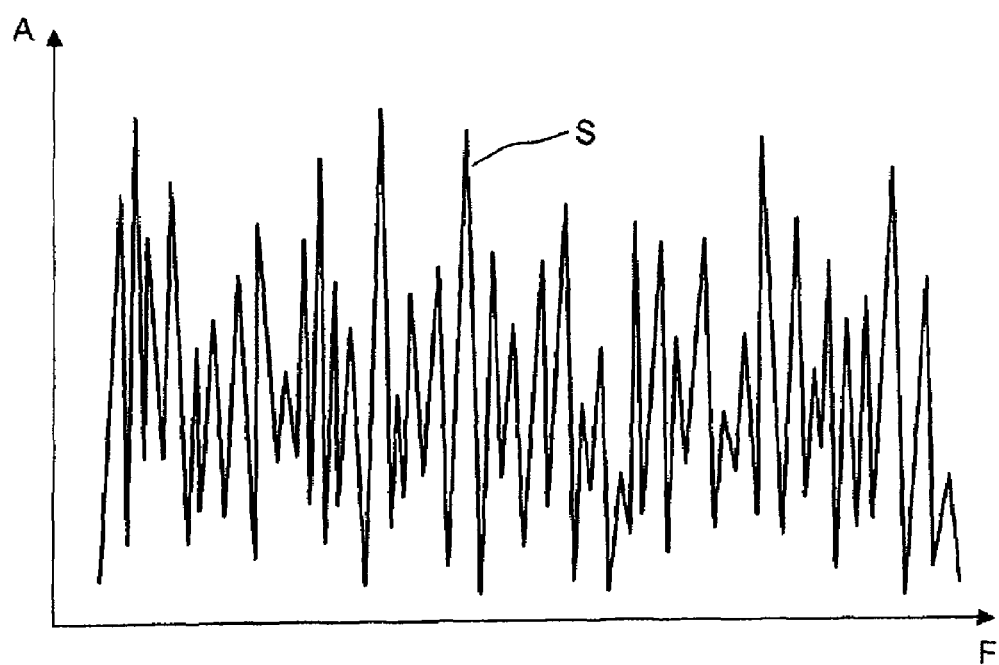
FIG. 5 represents the frequency signal obtained on the receiver.

The duly obtained temporal signal is difficult to digitize through an analog-digital converter. Also, to facilitate electronic implementation, a frequency ramp is generated to correspond to the spectral components of the pulsed signal and the transmitted power S is measured for each frequency. Mathematically, the measured signal includes only the power information, the phase information being lost, and it corresponds to the Fourier transform of the self-correlation of the percussive response of the enclosure. As an example, the amplitude A of this signal S as a function of the frequency F is shown in FIG. 5.

Figure 6:
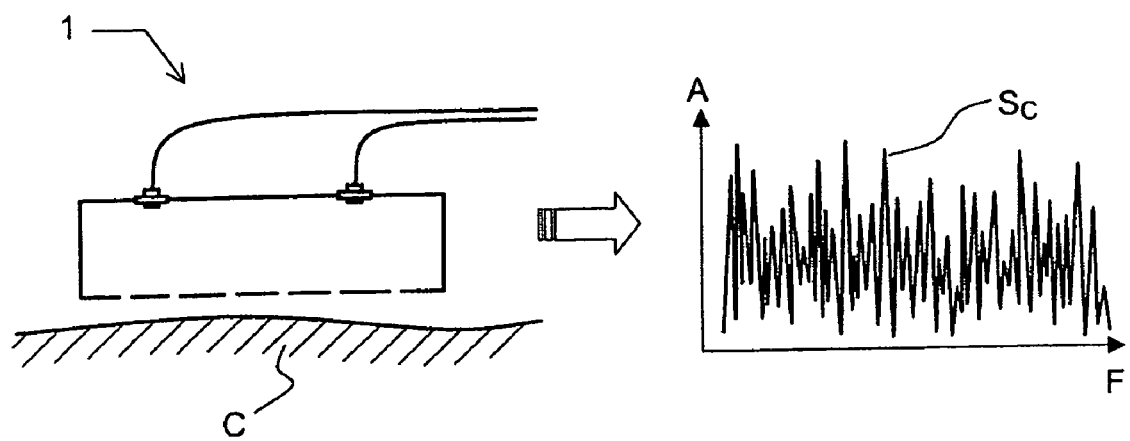
FIGS. 6 and 7 represent the signal variations in the presence or absence of an object in front of a hole of the enclosure.
Figure 7:
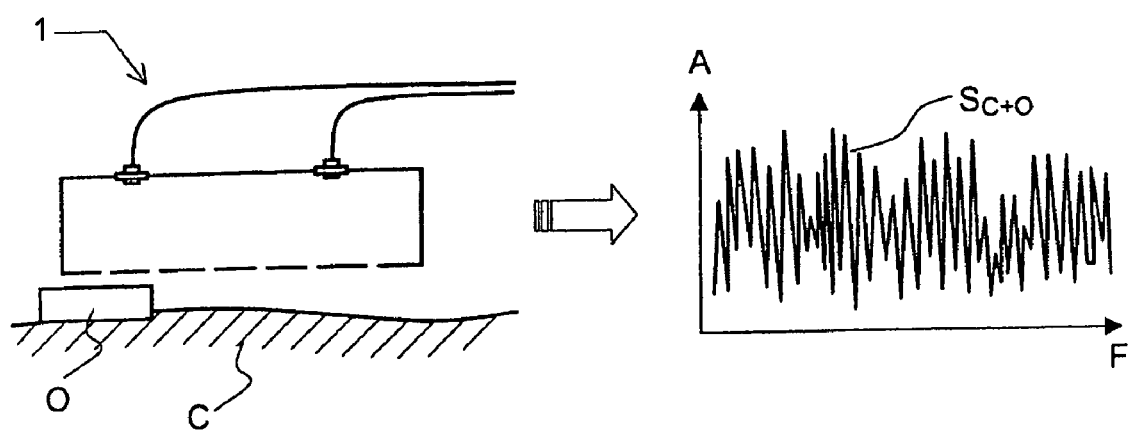

FIGS. 6 and 7 show the variations of the frequency signal S as a function of the presence or absence of an object O on a body C. Frequency signals $S_C$ and $S_{C+O}$ are obtained. As such, the signals are still too complex to be easily used.

To obtain a signal processing that is both simple and effective, the method of detecting dielectric objects on a human body according to the invention includes at least the following successive steps:

Step 1: Production of prerecorded received signals corresponding to the various open or closed states of the holes;

Step 2: Positioning of the detector in the vicinity of a human body to be analyzed;

Step 3: Acquisition of the received signal corresponding to this location of the detector and processing of said received signal;

Step 4: Correlation of said processed signal with the various prerecorded signals;

Step 5: Transmission of a warning signal when the correlation ration between the processed signal and at least one of the prerecorded signals exceeds a critical threshold.

The correlation method makes it possible to simply obtain dependable information on the presence or absence of suspect objects.

Figure 8:
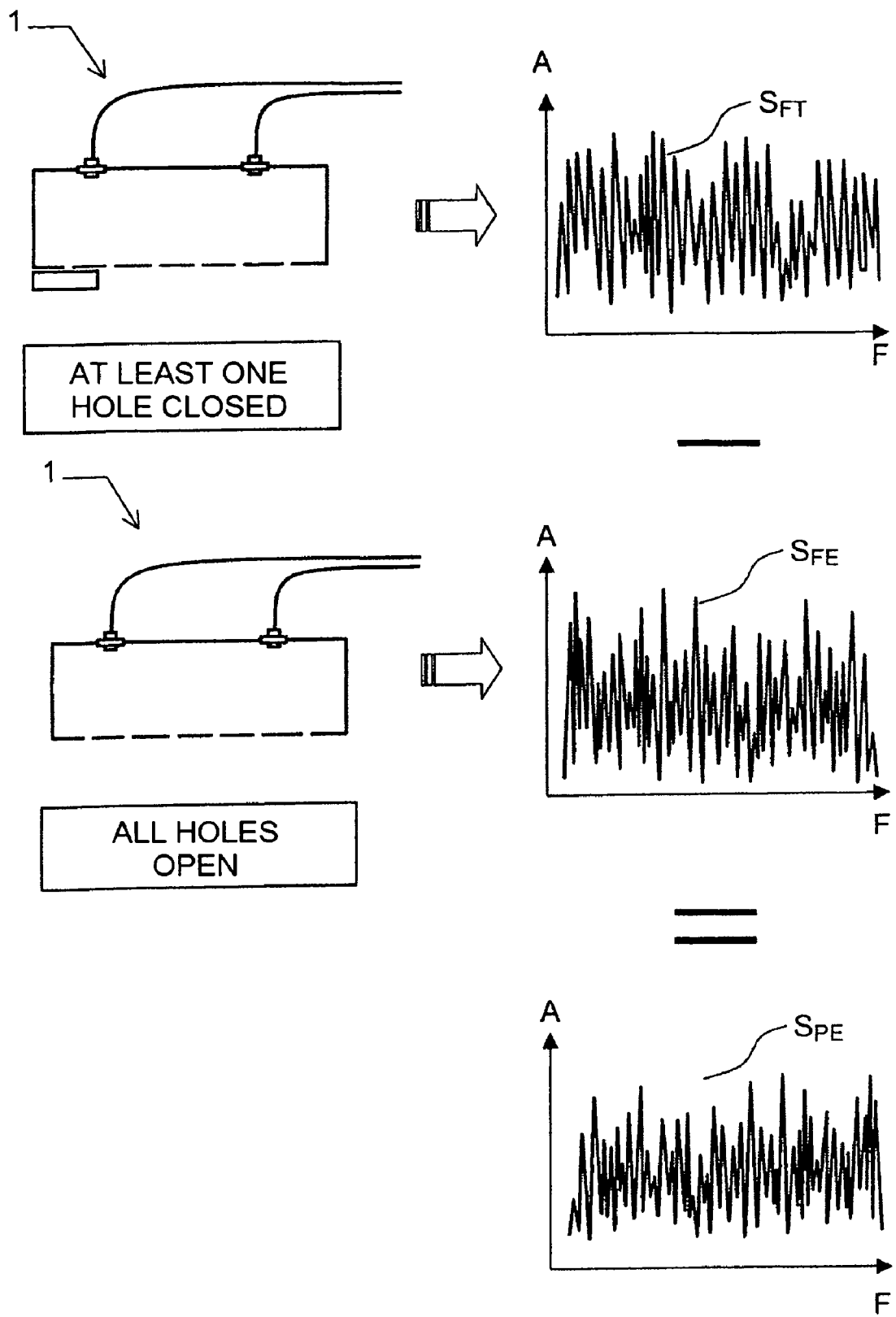
FIG. 8 represents the method of producing a prerecorded signal.

More specifically, the first step of the method includes the following substeps illustrated in FIG. 8:

Substep 1: With the holes of the enclosure all open, transmission of a transmission signal by the transmitter,

ALL HOLES OPEN box in FIG. 8;

Substep 2: Recording of the corresponding frequency signal, said signal being denoted enclosure-frequency-signal $S_{FE}$;

Substep 3: With at least one of the holes closed, transmission of a transmission signal by the transmitter,

AT LEAST ONE HOLE CLOSED box in FIG. 8;

Substep 4: Recording of the corresponding frequency signal, said signal being denoted hole-frequency-signal $S_{FT}$;

Substep 5: Calculation of a prerecorded signal $S_{PE}$ obtained by subtracting the enclosure-frequency-signal $S_{FE}$ from the hole-frequency-signal $S_{FT}$;

Substep 6: Execution of substeps 3 to 5 for the various open and closed states of the holes so as to obtain the various prerecorded signals.

A certain number of prerecorded signals are thus obtained, representing the signature of the open or closed states of the different holes.

Figure 9:
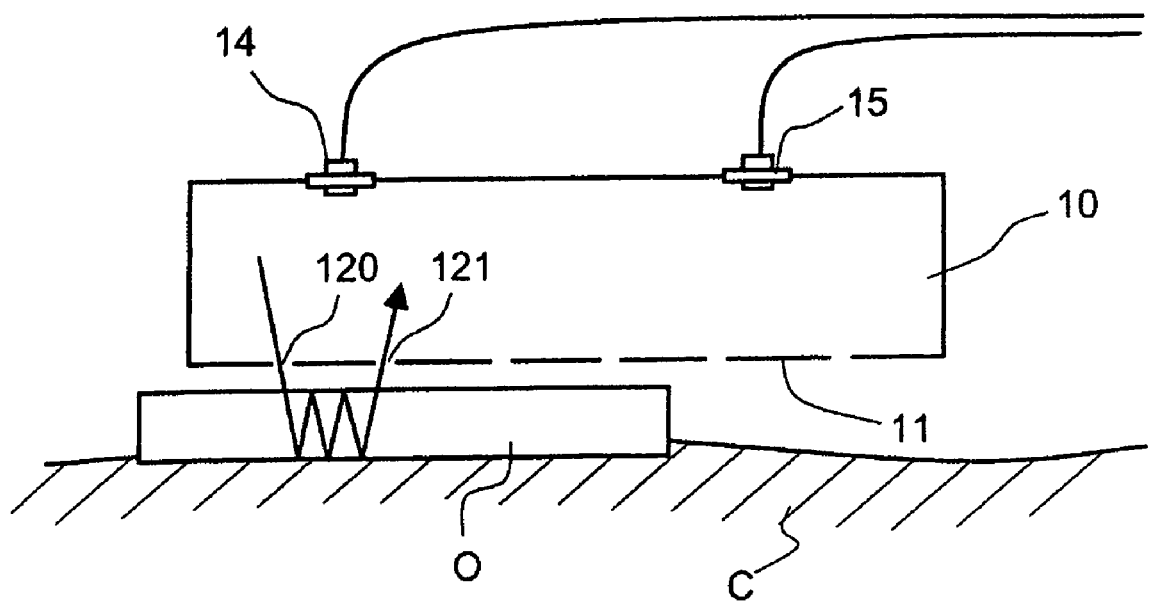
FIG. 9 represents the measurement of a dielectric object covering a number of holes of the enclosure.

It should be noted that the prerecorded signals need to represent at least all the configurations in which one hole is closed. Consequently, if the enclosure has N holes, at least N signals must be prerecorded. However, it is possible that certain bodies O, acting as dielectric guides, will link two holes together as illustrated in FIG. 9. In this case, a portion of the energy transmitted by the transmitter 14 leaving the box via the hole 120 in FIG. 9 will return via the hole 121 and will then be measured by the detector 15. Thus, the body O creates a correlation between the holes 120 and 121. It is, of course, possible to store prerecorded signals corresponding to this type of configuration.

The third step includes the following substeps:

Substep 1: Transmission of a transmission signal by the transmitter;

Substep 2: Recording of the frequency signal corresponding to said transmission signal, said signal being denoted measurement-frequency-signal;

Substep 3: Calculation of the processed signal obtained by subtraction of the enclosure-frequency-signal from the measurement-frequency-signal.

In the various steps and substeps of the method, the prerecorded and processed signals are obtained by subtraction of the enclosure-frequency-signal. This operation makes it possible to prevent the signal from the enclosure from disturbing the final measurement by introducing a spurious correlation linked to the enclosure.

The fourth step of the method is illustrated in FIGS. 10 and 11. In both cases, the processed signals $S_O$ obtained by measurement are correlated with the prerecorded signals $S_{PE1}$ and $S_{PE2}$. In these figures, the correlation operation is conventionally represented by a cross centered in a circle.

In FIG. 10, the measured signal is almost identical to the prerecorded signal $S_{PE1}$. In this case, the correlation ratio is high, which means that the measured signal is representative of a configuration that very closely approximates to the prerecorded signal, which corresponds, for example, to a certain closed hole.

In FIG. 11, the measured signal is different from the prerecorded signal $S_{PE2}$. In this case, the correlation ratio is low, which means that the measured signal is not representative of the configuration of the prerecorded signal, which corresponds, for example, to a certain closed hole.

By comparing the processed signal to all the prerecorded signals, any correlations are revealed. Thus, it becomes possible to detect hidden objects by this method.

To implement this method, the device includes an electronic data processing system comprising means:

Of memorizing prerecorded signals corresponding to the various open or closed states of the holes;

Of acquiring the signals received by the detector;

Of processing said received signals;

Of correlating said processed signals with the different prerecorded signals;

Of warning when the correlation ratio between a processed signal and at least one of the prerecorded signals exceeds a critical threshold, said warning means being audible or visual.

The computation power needed to process the signals is not great. If it is assumed that a human operator moves the structure at a speed of 1 meter/second and that a resolution of around a centimeter is required, it is enough for the system to be able to take measurements at a rate of 100 Hertz, or one measurement every 10 milliseconds. Now, each signal can be digitized on 1000 points. If a hundred correlations with prerecorded signals are done, 100 000 operations must be carried out between two measurements, or 100 000 operations in 10 milliseconds. Each operation must be carried out at a minimum frequency of 10 Megahertz, which is very low using current computation means.

Figure 12:
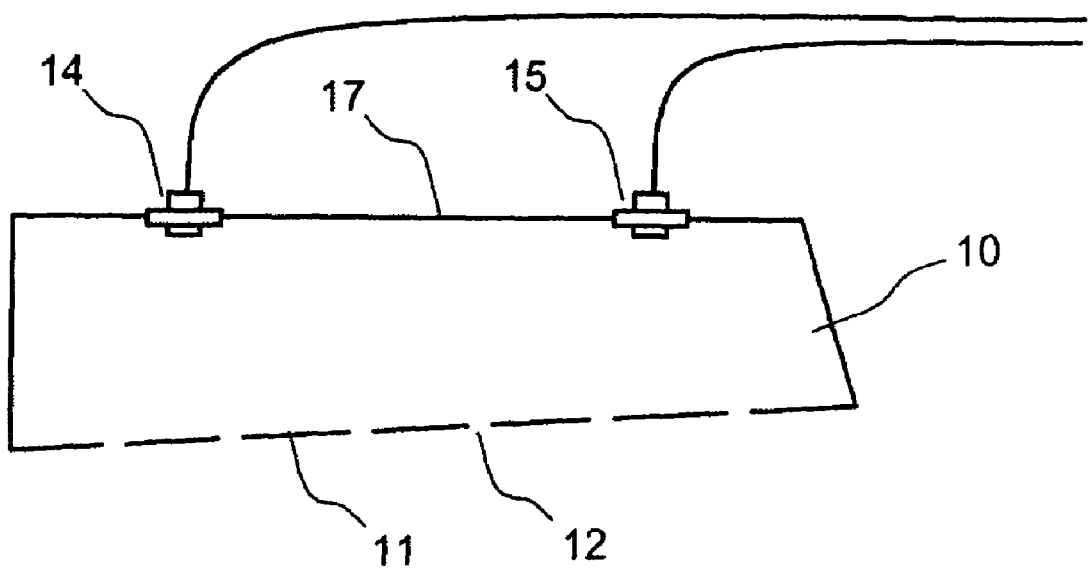
FIGS. 12, 13, 14 and 15 represent four variants of embodiments of the enclosure.
Figure 13:
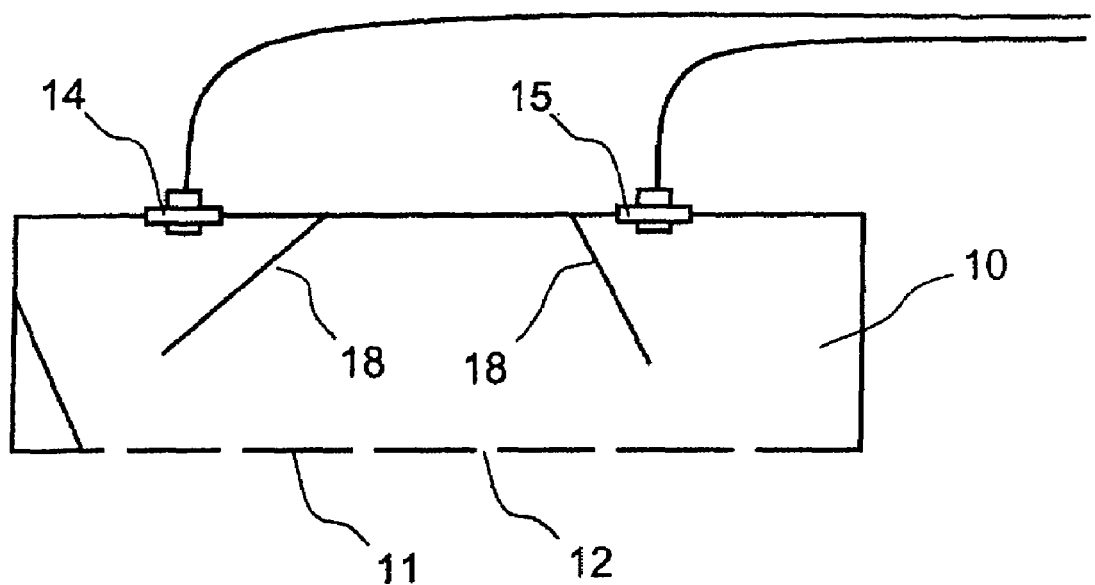

As has been stated, one of the important points of the device is that the geometry of the enclosure is chaotic. To this end, a first simple solution consists in avoiding having the main surfaces of the enclosure parallel. FIG. 12 illustrates this configuration in which the surface 17 is not parallel to the measurement surface 12, the two surfaces being substantially flat. Another possible arrangement is illustrated in FIG. 13. In this case, deflectors 18 introduced into an enclosure 10 of simple shape make the latter chaotic. These deflectors can be positioned between transmitter and receiver, for example.

Similarly, the signals are sensitive to the deformations of the enclosure. It is therefore essential to choose an enclosure structure that is both rigid and insensitive to the thermal variations. For a cavity with dimensions measuring a few centimeters, the deformations must not exceed a few microns.

Figure 14:
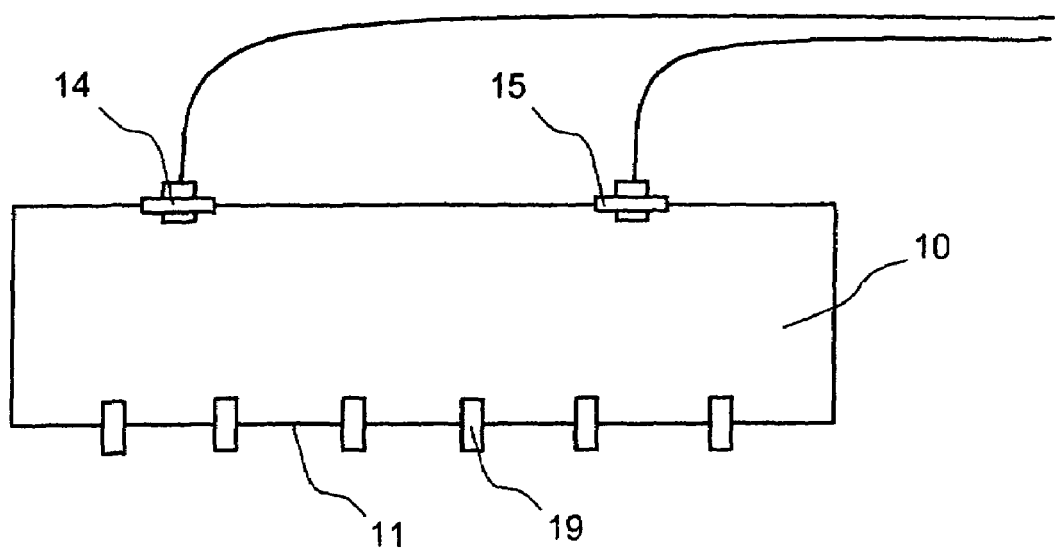

An equally important point is that the electromagnetic energy can exit via the holes in quantities sufficient for the difference between an open or closed hole to be significant. To avoid having holes that are too big, a possible solution is illustrated in FIG. 14. Waveguides 19 are placed in line with the holes to facilitate the losses. These guides can be dielectric or coaxial guides.

Figure 15:
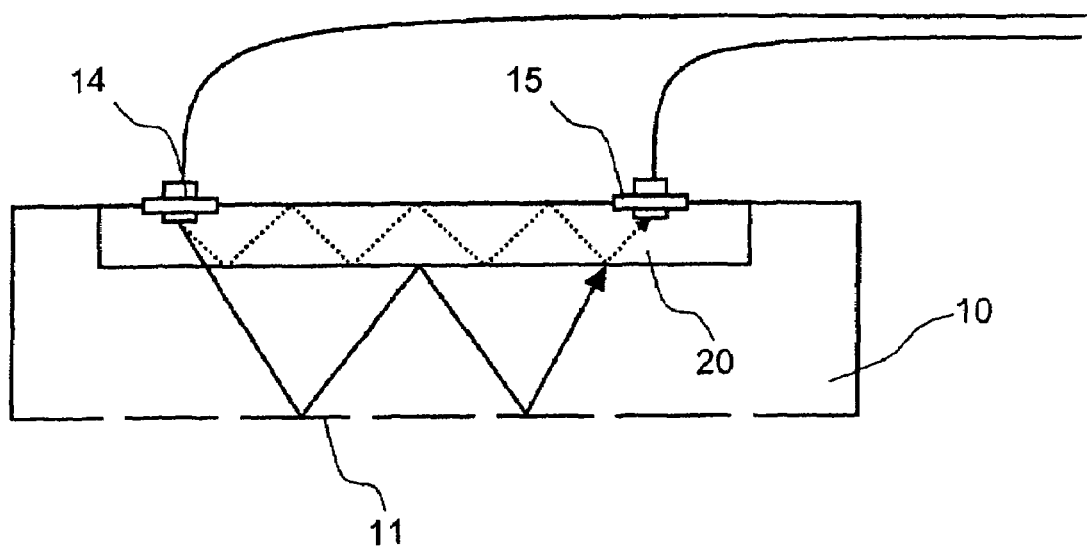

It has also been seen how the received signal includes only signal amplitude or intensity information, the phase information being lost. To improve the processing and refine the measurements, the latter information can prove interesting. A simple means of obtaining it is illustrated in FIG. 15. A waveguide 20 sends from the transmitter to the receiver a reference wave. The interferences of this reference wave with the measured wave are used to determine the relative phase between these two waves. Since the phase information is known to within a constant, it then becomes possible to carry out a Fourier transform of the percussive response of the enclosure. This method is similar to that implemented to perform a holographic recording in which the interferences between a measurement wave and a reference wave are used to record on one and the same medium the phase and intensity of the optical measurement wave.

FIG. 16 represents a device for detecting objects O on a subject C according to the invention. A suspect object is concealed on the subject C. The device essentially comprises:

A structure 1 including the system for transmitting and receiving microwave frequency signals;

a system 2 for processing the received signals possibly including alarm means 22 in case suspect objects are detected, represented by a circle on the box 2 in FIG. 16.

The use of the device is very simple. A security agent, not shown in FIG. 1, scans the body of the person to be checked.

In the top part of the figure, no suspect object is located under the holes of the structure. The measured signal cannot be correlated with any of the prerecorded signals. The alarm is not activated.

In the bottom part of FIG. 16, the suspect object is located under the holes of the structure. In this case, the measured signal corresponds to at least one of the prerecorded signals. The alarm 22 is activated.

What is claimed is:

1. A device for detecting dielectric objects on a human body comprising:
    a detector with an enclosure in which are disposed a wave transmitter transmitting a microwave frequency signal and a microwave frequency receiver, said enclosure including a measurement surface intended to be positioned in the vicinity of said human body, wherein said enclosure is highly reflective to the waves transmitted by the transmitter, has a chaotic type geometry for said waves and wherein the measurement surface includes at least two holes, wherein the dimensions of the cavity of the enclosure measuring a few centimeters.

2. The detection device as claimed in claim 1, wherein the structure includes a single transmitter also serving as the receiver.

3. The detection device as claimed in claim 1, wherein the enclosure has essentially flat walls.

4. The detection device as claimed in claim 3, wherein flat reflectors are disposed inside the enclosure.

5. The detection device as claimed in claim 4, wherein a dielectric guide links the transmitter and the receiver so as to provide a reference signal to the receiver.

6. The detection device as claimed in claim 3, wherein a dielectric guide links the transmitter and the receiver so as to provide a reference signal to the receiver.

7. The detection device as claimed in claim 1, wherein waveguides are disposed in line with the holes to facilitate the leakage of the waves transmitted by the transmitter towards the outside of the enclosure.

8. The detection device as claimed in claim 1, wherein the structure is portable and includes, a handle.

9. The detection device as claimed in claim 1, wherein the spectrum of the transmitted signal is located in the 18 to 40 gigahertz frequency range.

10. The detection device as claimed in claim 1, wherein the device also includes a data processing system comprising:
    memorizing means prerecording signals corresponding to the various open or closed states of the holes;
    acquiring means for receiving the signals received by the detector;
    processing means for processing said received signals;
    correlating means for correlating said processed signals with the various prerecorded signals;
    warning means for warning when the correlation ratio between a processed signal and at least one of the prerecorded signals exceeds a critical threshold, said warning means being audible or visual.

11. A method of detecting dielectric objects on a human body from a detection device as claimed in claim 10, comprising the following steps:
    producing of prerecorded received signals $S_{PE}$ corresponding to the different open or closed states of the holes;
    positioning of the detector in the vicinity of a human body to be analyzed;
    acquiring of the received signal corresponding to this location of the detector and processing of said received signal;
    correlating of said processed signal with the various prerecorded signals $S_{PE}$, transmitting of a warning signal when the correlation ratio between the processed signal and at least one of the prerecorded signals exceeds a critical threshold.

12. The detection method as claimed in claim 10, wherein said producing step includes the following substeps:
with the holes of the enclosure all open, transmission of a frequency ramp by the transmitter;
recording of the received signal denoted enclosure-frequency-signal $S_{PE}$ corresponding to said transmission signal;
with at least one of the holes closed, transmitting of a frequency ramp by the transmitter;
recording of the received frequency signal denoted hole-frequency-signal $S_{FT}$ corresponding to said transmission signal;
calculating of a prerecorded signal $S_{PE}$ obtained by subtraction of the enclosure-frequency-signal $S_{FE}$ from the hole-frequency-signal $S_{FT}$;
executing said transmitting, recording and calculating steps for the various open or closed states of the holes so as to obtain the various prerecorded signals.

13. The detection method as claimed in claim 12, wherein the third step includes the following substeps:
transmitting of a frequency ramp by the transmitter;
recording of the received frequency signal called measurement-frequency-signal corresponding to said transmission signal;
calculating of the processed signal obtained by subtraction of the enclosure-frequency-signal from the measurement-frequency-signal.

14. The detection method as claimed in claim 11, wherein the third step includes the following substeps:
transmitting of a frequency ramp by the transmitter;
recording of the received frequency signal called measurement-frequency-signal corresponding to said transmission signal;
calculating of the processed signal obtained by subtraction of the enclosure-frequency-signal from the measurement-frequency-signal.

* * * * *